United States Patent [19]

Peltier et al.

[11] Patent Number: 5,429,504
[45] Date of Patent: Jul. 4, 1995

[54] TWIST DRILLS FOR BONE SURGERY, IN PARTICULAR FOR DENTAL SURGERY

[76] Inventors: Patrick Peltier; Guy Peltier, both of rue des Lilas, 92500 Rueil-Malmaison, France

[21] Appl. No.: 139,724

[22] Filed: Oct. 22, 1993

[51] Int. Cl.⁶ .................................. A61C 3/02
[52] U.S. Cl. .................................... 433/165
[58] Field of Search ............... 433/165, 166, 102, 72; 606/80

[56] References Cited

U.S. PATENT DOCUMENTS

| | | | |
|---|---|---|---|
| 4,345,899 | 8/1982 | Vlock | 433/165 |
| 4,431,416 | 2/1984 | Niznick | 433/174 |
| 4,474,556 | 10/1984 | Ellis et al. | 433/173 |
| 4,820,156 | 4/1989 | Ross | 433/173 |
| 5,035,617 | 7/1991 | McSpadden | 433/102 |
| 5,261,818 | 11/1993 | Shaw | 433/165 |

FOREIGN PATENT DOCUMENTS

| | | | |
|---|---|---|---|
| 0515274 | 11/1992 | European Pat. Off. | 433/165 |
| 2613212 | 10/1988 | France | 433/72 |
| 2059778 | 4/1981 | United Kingdom | 433/102 |

*Primary Examiner*—Cary E. O'Connor
*Attorney, Agent, or Firm*—Larson and Taylor

[57] ABSTRACT

The drill consists of a cylindrical body (1) in which at least two helical flutes (2) are hollowed out, which helical flutes (2) delimit as many helical cutting edges (3), this body (1) being extended via a drive shank (4). The body (1) is equipped with guide marks consisting of circumferential grooves (7), having a profile substantially in the shape of an arc of a circle, which are formed in the cylindrical body (1), and of an elastic ring (8, 9 or 10) which has a profile adapted to that of the grooves (7) and a more or less toric shape and which is capable of being placed, as desired, in one or other of these grooves (7), before the drill is put into operation, and of remaining therein until completion of this operation.

7 Claims, 3 Drawing Sheets

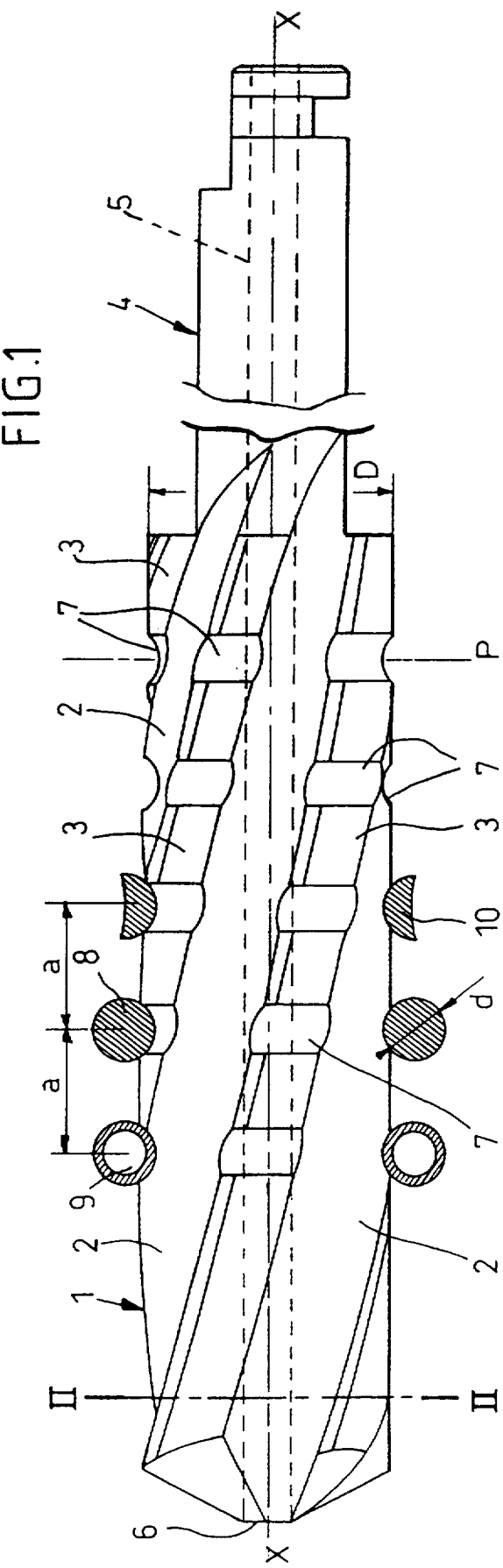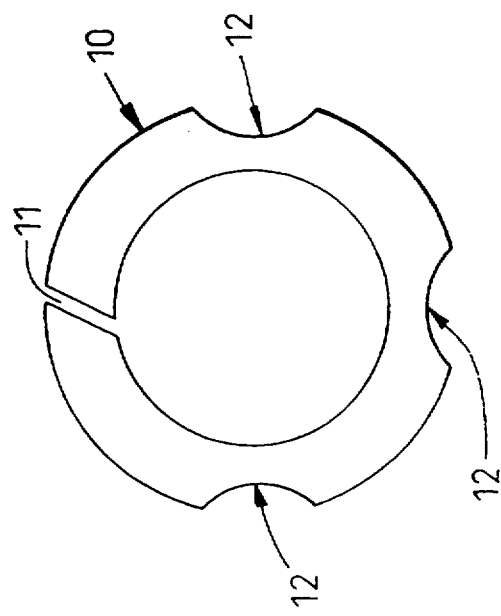

TWIST DRILLS FOR BONE SURGERY, IN PARTICULAR FOR DENTAL SURGERY

The invention relates to twist drills for bone surgery, and it concerns more particularly, but not exclusively, drills for dental surgery, that is to say drills intended for boring or reaming, in the human jawbone, seats for dental implants.

It is known that these drills consist of a cylindrical body in which at least two, and generally two to four, helical flutes are hollowed out, which helical flutes delimit as many helical cutting edges. This body is extended via a shank intended to be fixed in a drill chuck or mandrel which, when operating, communicates to the drill its rotational movement.

It is also known that, in bone surgery, the practitioner must stop the drill as precisely as possible at the desired depth, which is generally determined beforehand by radiography. In particular, in prosthetic dental surgery, the seat or hole to be formed in the jawbone must have a depth which is sufficient to ensure that the cylindrical implant (made of titanium, screwed or smooth) to be inserted therein has a strong anchoring, but which is limited to a value which prevents it from opening into the maxillary sinus. In general, the practitioner does not have available any guide mark allowing him to reach the desired depth with safety in a single attempt, and he is therefore obliged to make several attempts with the same drill, measuring the depth of penetration of this drill between each pass and comparing it then with the desired value. In order to facilitate the work of the practitioner, some drills have on their cutting edges, at uniform axial spacings, guide marks consisting of V-shaped notches of small radial depth (0.1 mm approximately), but it is difficult for the practitioner not to confuse two successive notches when his working, especially when he has to operate on the posterior area of the jaw of a patient, a procedure in which these notches do not afford the necessary safety.

Similar disadvantages arise in general bone surgery, for example when implanting a pin. In order to eliminate these disadvantages, it has been proposed (DE-A-3,800,482) to equip the drill with penetration guide marks which comprise circumferential grooves, having a profile substantially in the shape of an arc of a circle, distributed at predetermined axial spacings, and which act by coming into contact with the bone to be treated, but, in this known construction, a sleeve of material is arranged around the drill and is immobilized by introducing balls into the grooves which are formed in the drive shank, and it is the lower end of this sleeve coming into contact with the bone to be treated which indicates that the desired depth of penetration has been reached. The disadvantages of this known drill are that it is complicated and expensive, insufficiently precise, and difficult to sterilize.

The object of the invention is to overcome the above-mentioned disadvantages by providing the drills with guide marks which are adjustable and clearly visible under the most difficult operating conditions, and to do this without appreciably modifying the customary shape of the drills and, consequently, the method for manufacturing these drills, and without significantly increasing their cost price.

To this end, the invention relates to a twist drill for bone surgery, in particular for dental surgery, consisting of a cylindrical body in which at least two helical flutes are hollowed out, which helical flutes delimit as many helical cutting edges, this body being extended via a drive shank, and the drill being equipped with penetration guide marks which comprise circumferential grooves, having a profile substantially in the shape of an arc of a circle, distributed at defined axial spacings, and which act by coming into contact with the bone or the tooth to be treated, wherein the grooves are formed in the cylindrical body and are designed to receive an elastic ring which has a profile adapted to that of the grooves and a more or less toric shape and which is capable of being placed, as desired, in at least one or other of these grooves, before the drill is put into operation, and of remaining therein until completion of this operation, said completion being determined by the ring coming into contact with the bone or the tooth to be treated.

Each circumferential groove thus formed in the body of the drill is of course divided into sections by the helical flutes. In other words, it affects only the cutting edges, but constitutes, by means of all of its successive sections, a seat capable of holding the elastic ring which may be placed therein.

As regards dental surgery drills in which the external diameter of the body is generally not more than 4 mm, the elastic ring is preferably given an external diameter, in transverse section, of the order of 1 mm and the annular grooves are preferably given uniform mutual spacings of between 1 and 2 mm, for example equal to 2 mm. According to a preferred embodiment, these grooves are situated respectively at 8, 10, 12, 14, 16, 18 and 20 mm from that end of the drill opposite the shank.

The elastic ring is preferably made of rubber or plastic whose composition, homologized in the application envisaged, is capable of withstanding the sterilization conditions as well as the heat due to the working of the drill and the possible contact with the bone to be drilled, such as a jawbone. The ring can nevertheless also be made of spring stainless steel and can consist, for example, of a helical spring closed on itself in ring shape by screwing one of its ends into the other.

The invention will now be described in greater detail with the aid of the attached drawings.

FIG. 1 of these drawings shows, in elevation, a drill which is established in accordance with the invention and on which are placed three different types of elastic rings, only one ring of course having to be put into position under the actual use conditions.

FIG. 5 shows, in transverse section through its plane of symmetry, one of the rings in FIG. 1.

Figure 4:
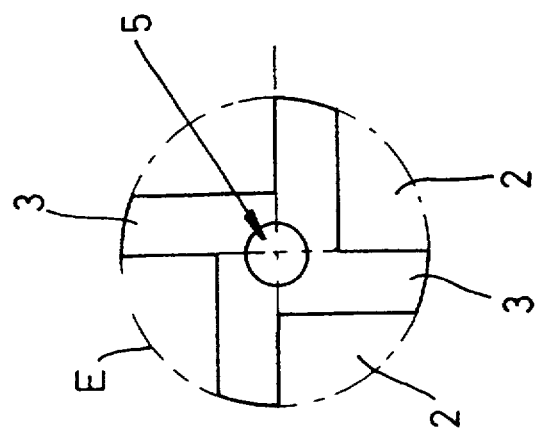
FIGS. 3 and 4 show, in transverse sectional views similar to that in FIG. 2, reamer drills having three and four cutting edges, respectively.

As is shown diagrammatically in FIG. 1, a drill for dental surgery consists of a cylindrical body 1 in which at least two helical flutes 2 are hollowed out, which helical flutes 2 delimit as many helical cutting edges 3. The body 1 is extended via a drive shank 4. The body 1 and the shank 4 are generally equipped with a longitudinal irrigation channel 5.

Figure 3:
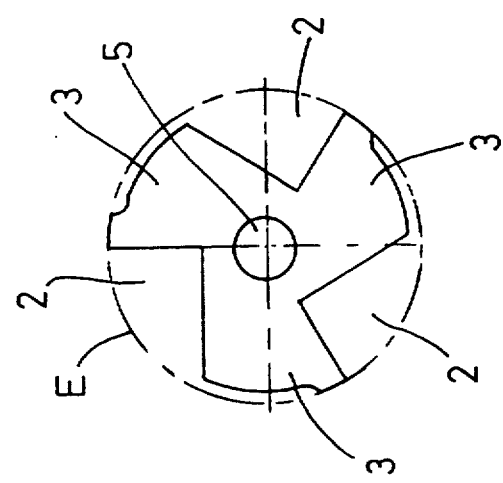
Figure 2:
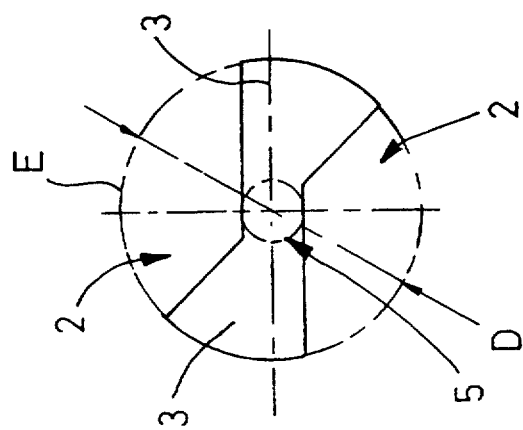
FIG. 2 shows a bore drill, in transverse section along the line II—II in FIG. 1.

It may be a bore drill, having two flutes 2 and two cutting edges 3, as shown in FIG. 2, in which case the irrigation channel 5 is blind but opens out via radial passages. It may also be a reamer drill having three flutes 2 and three cutting edges 3, as shown in FIG. 3, in which case the irrigation channel 5 opens out at the free end 6 of the drill, that is to say at that end opposite the shank 4. The reamer drill in FIG. 4 differs from that in FIG. 3 essentially in terms of the number of flutes 2 and cutting edges 3, which is here equal to four. In the above text, when the body 1 has been described as "cylindrical", this has meant a body whose geometric envelope E is cylindrical as indicated in dot-and-dash lines in each of FIGS. 2 to 4.

This being the case, according to the invention and as shown in FIG. 1, the body 1 is equipped with circumferential grooves 7, having a profile substantially in the shape of an arc of a circle, each admitting a plane of symmetry, such as P, perpendicular to the longitudinal axis X—X of the drill, which axis constitutes the axis of rotation of the drill and the axis of revolution of the envelope E. In addition, each drill has an elastic ring, such as 8, 9 or 10, which has a profile adapted to that of the grooves 7 and a more or less toric shape and which is capable of being placed, as desired, in one or other of these grooves 7. As has been set out hereinabove, it will be seen from FIG. 1 that each groove 7 is divided into successive sections by the flutes 2 but constitutes a reliable seat for an elastic ring having the shape of a continuous circle, or even of a circle exhibiting a narrow radial slot, such as that shown at 11 in FIG. 5.

The body 1 of the drill for dental surgery shown in FIG. 1 has an external diameter D (or diameter of the directrix of its envelope E, see FIG. 2) which is generally not more than 4 mm. In this case, the elastic ring, such as 8, is preferably given an external diameter d, in transverse section, of the order of 1 mm. This means that the radius of curvature of the cross section of the grooves 7 through a plane passing through the axis X—X is of the order of 0.5 mm.

The grooves 7 are arranged at uniform mutual spacings "a" of between 1 and 2 mm, preferably equal to 2 mm. Although FIG. 1 shows a smaller number of grooves 7, it is furthermore preferable that these are situated advantageously at 8, 10, 12, 14, 16, 18 and 20 mm from the free end 6 of the drill (spacings measured from the respective planes of symmetry P defined hereinabove).

FIG. 1 shows at 8 a toric ring made of flexible plastic or rubber; at 9 a ring consisting of a helical spring whose final turns are screwed into one another, and at 10 (see also FIG. 5) a tubular ring made of spring stainless steel equipped with the abovementioned slot 11 and notches 12 facilitating its bending.

Figure 6:
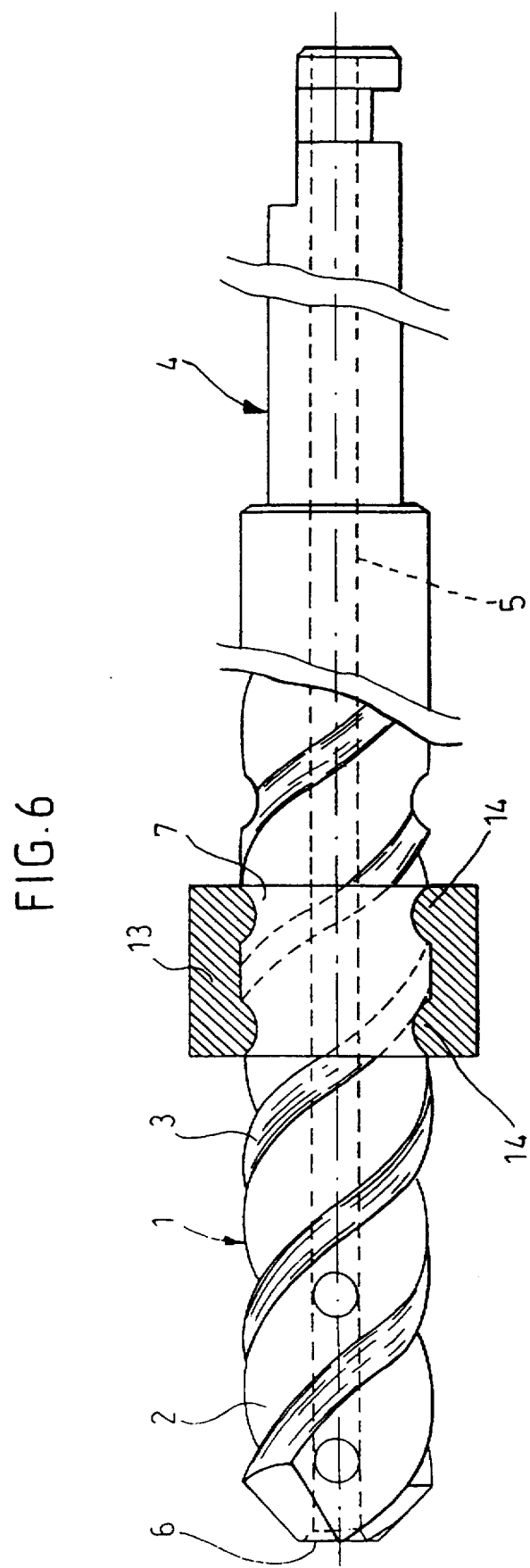
FIG. 6 shows a variant of the embodiment in FIG. 1.

According to the variant in FIG. 6, the ring 13, which is made of flexible plastic or rubber, has two continuous internal beads 14, whose axial spacing is equal to the spacing "a" between grooves 7, this allowing it to be engaged in two consecutive grooves and improving the retention of the ring 13.

A drill for dental surgery is thus obtained, whose operation is as follows.

In a known manner, the bore drill in FIG. 2, whose diameter is generally between 2.1 and 2.9 mm, is first used, after placing one of the rings, such as 8 to 10, on the drill in one of its grooves 7 corresponding to the length of the implant to be inserted in the bone. The reamer drill in FIG. 3 is then used, followed, if appropriate, by that in FIG. 4 (drills whose respective diameters are between that of the bore drill and 4 mm), after likewise having placed a ring in one of the grooves 7. According to a variant (not shown), it is possible to provide a combined drill for both boring and reaming, in which case it suffices, taking as a basis the embodiment in FIG. 1, to shorten the body 1 and to arrange, between the shank 4 and the body 1 thus shortened, a reamer drill body of greater diameter than this body 1, this making it possible to carry out the boring and reaming operations with the same drill. Once these boring and reaming operations have been completed, it is possible to screw or insert with force the appropriate implant. The drills which are to be used for these operations are cleaned and sterilized, together with their ring put into position beforehand, in the medical apparatuses adapted to the current hygiene standards.

The intrinsic elasticity of the ring chosen allows the practitioner anyway to move the ring from one groove 7 (or a pair of grooves 7, in accordance with the variant in FIG. 6) to the other, as far as the groove (or pair of grooves) corresponding to the desired working depth, but holds it subsequently in this last groove (or pair of grooves) during the sterilization operations, and then the boring or reaming operations. Once in position, the ring constitutes an accurate and clearly visible guide mark, regardless of the instantaneous angular position and the speed of rotation of the drill.

Although the drill according to the invention has been described with reference to its application in dental surgery, it goes without saying that it can just as readily be used in general bone surgery.

We claim:

1. A twist drill assembly for bone surgery, in particular for dental surgery, comprising a twist drill and an elastic ring, said twist drill consisting of a cylindrical body in which at least two helical flutes are hollowed out, which helial flutes delimit as many helical cutting edges, this body being extended via a drive shank (4) and said drill being equipped with penetration guide marks which comprise circumferential grooves having a profile substantially in the shape of an arc of a circle, distributed at defined axial spacings, and which act by coming into contact with the bone or the tooth to be treated, said grooves being formed in said cylindrical body to cross said flutes and being designed to receive said elastic ring which has a profile adapted to that of said grooves and a more or less toric shape and which is capable of being placed in at least one or other of these grooves, before said drill is put into operation, and of remaining therein until completion of this operation, determined by said ring coming into contact with the bone or the tooth to be treated.

2. The drill assembly for dental surgery as claimed in claim 1, wherein the diameter of said body is not more than 4 mm, and wherein said elastic ring has an external diameter, in transverse section, of the order of 1 mm.

3. The drill assembly as claimed in claim 2, wherein said annular grooves are arranged at uniform mutual spacings of between 1 and 2 mm.

4. The drill assembly as claimed in claim 3, wherein said annular grooves are arranged at mutual spacings of 2 mm.

5. The drill as claimed in claim 4, wherein said grooves are situated respectively at 8, 10, 12, 14, 16, 18 and 20 mm from that end of said drill opposite said shank.

6. The drill assembly as claimed in claim 1, wherein said ring is made of rubber or plastic whose composition, homologized in the application envisaged, is capable of withstanding the sterilization conditions as well as the heat due to the working of said drill and to the possible contact with the bone to be drilled, such as a jawbone.

7. The drill assembly as claimed in claim 1, wherein said ring is made of spring stainless steel.

* * * * *